US00PP25183P3

(12) United States Plant Patent
Bentley

(10) Patent No.: US PP25,183 P3
(45) Date of Patent: Dec. 16, 2014

(54) *SALVIA* PLANT NAMED 'SAL010-1'

(50) Latin Name: ***Salvia* hybrid**
Varietal Denomination: SAL010-1

(71) Applicant: Howard Bentley, Wonga Park (AU)

(72) Inventor: Howard Bentley, Wonga Park (AU)

( * ) Notice: Subject to any disclaimer, the term of this patent is extended or adjusted under 35 U.S.C. 154(b) by 99 days.

(21) Appl. No.: 13/815,340

(22) Filed: Feb. 22, 2013

(65) Prior Publication Data

US 2014/0245515 P1 Aug. 28, 2014

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Cassandra Bright

(57) ABSTRACT

A new and distinct *Salvia* hybrid cultivar named 'SAL010-1' is disclosed, characterized by unique flower and calyx color as well as deep red bud color. Additionally 'SAL010-1' can be characterized by medium to dense plant density and a long flowering season. The new variety is a *Salvia*, typically produced as an outdoor ornamental plant.

2 Drawing Sheets

Latin name of the genus and species: *Salvia* hybrid.
Variety denomination: 'SAL010-1'.

BACKGROUND OF THE INVENTION

The new cultivar is the product of chance discovery. The new variety originated as a naturally occurring whole plant mutation of the commercial variety of *Salvia* hybrid 'Wendy's Wish' U.S. Plant Pat. No. 21,889.

The new variety was discovered by the inventor, Howard Bentley, a citizen of Australia, during October of 2010 in a commercial greenhouse belonging to the inventor in Wonga Park, Australia. After identifying the new variety as a potentially interesting selection, the inventor continued confidential testing and propagation of 'SAL010-1' assessing stability of the unique characteristics of this variety.

Asexual reproduction of the new cultivar 'SAL010-1' was first performed at a nursery in Wonga Park, Australia, by vegetative cutting in September of 2011. Access to all plants was restricted, as plants were kept in a location that is not open to the public. Through subsequent propagation by vegetative cuttings, six generations have been reproduced, which have shown that the unique features of this cultivar are stable and reproduced true to type.

SUMMARY OF THE INVENTION

The cultivar 'SAL010-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAL010-1.' These characteristics in combination distinguish 'SAL010-1' as a new and distinct *Salvia* hybrid cultivar:

1. Bright mid to deep red/pink flower color.
2. Calyx color distinctive salmon/bronze.
3. Plant density is moderate to dense.

4. Deep red bud color.
5. Long flowering season.

PARENT COMPARISON

Plants of the new cultivar 'SAL010-1' are similar to the parent, *Salvia* hybrid 'Wendy's Wish' in most horticultural characteristics. The new variety, however, produces a different flower color than parent 'Wendy's Wish'. Additionally 'SAL010-1' produces different calyx color than parent 'Wendy's Wish'.

COMMERCIAL COMPARISON

Plants of the new cultivar 'SAL010-1' are most similar to the parent variety. The inventor is unaware of other commercial varieties to make an effective comparison.

BRIEF DESCRIPTION OF THE PHOTOGRAPHS

Figure 1:
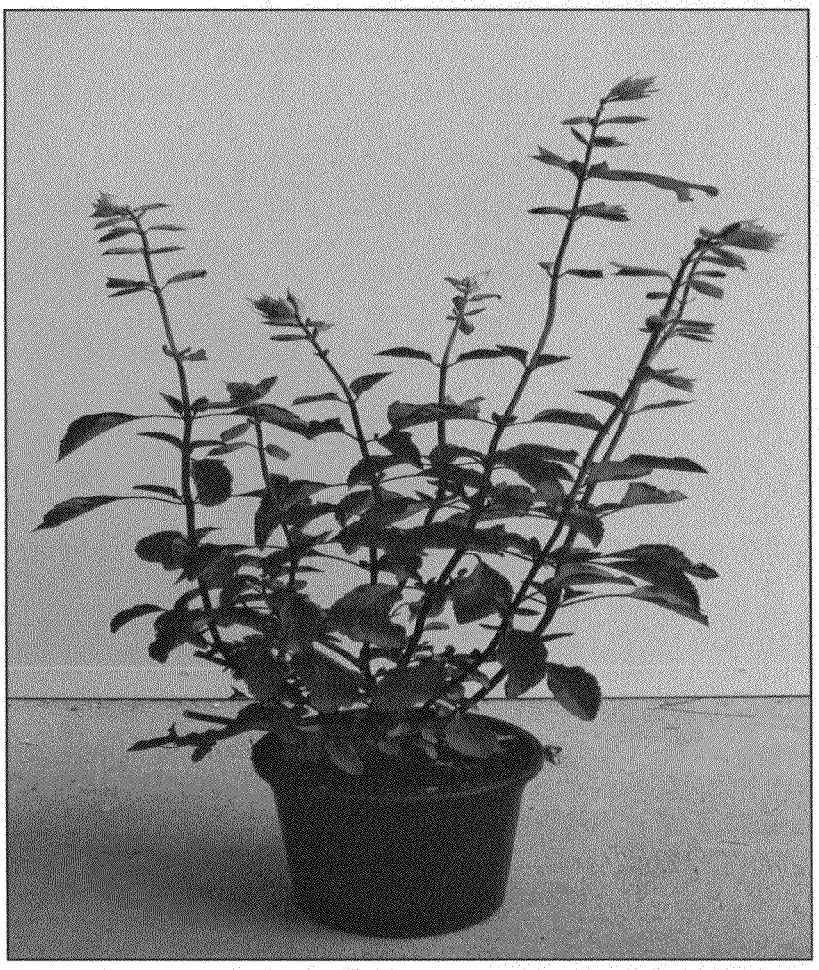

The accompanying photograph in FIG. 1 illustrates in full color a typical plant of 'SAL010-1' grown in a commercial greenhouse in Wonga Park Australia. This plant is approximately 21 weeks old, shown planted in a 17 cm. container.

Figure 2:
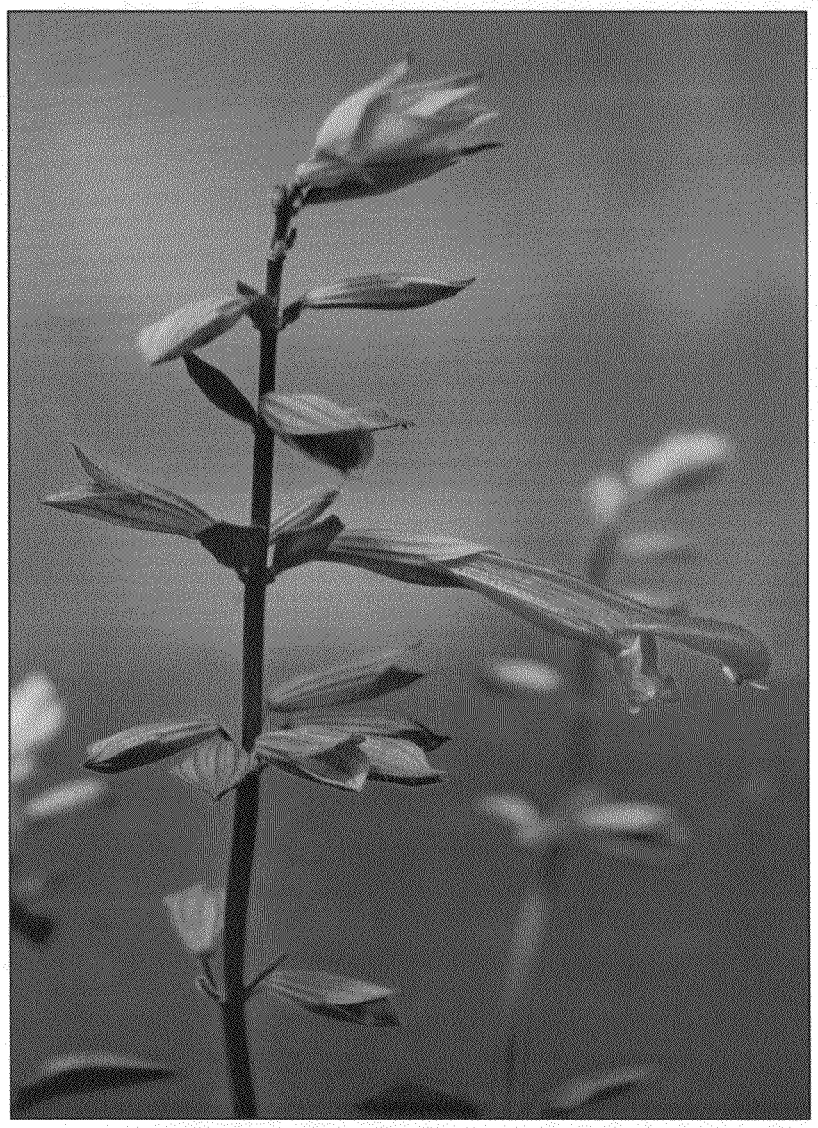

FIG. 2 illustrates in full color a close up of the flowers of 'SAL010-1'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SAL010-1' plants grown in a greenhouse in Wonga Park, Australia. Plants are approximately 22 weeks old. Temperatures ranged from 15° C. to 22° C. day and night. No artificial light, photoperiodic treatments were given to the plants. No chemical treatments were given to plants. Measurements and numerical values represent averages of typical plant types.
Botanical classification: *Salvia* hybrid 'SAL010-1'.

PROPAGATION

Time to initiate roots: About 10-14 days at approximately 20-21° C.
Time to produce a rooted cutting: About 21-28 days at 20-21° C.

PLANT

Age of plant described: Approximately 21 weeks from a rooted cutting.
Height: Approximately 90 cm. (at maturity).
Plant spread: Approximately 80 cm. (at maturity).
Growth rate: Moderate to fast.
Length of primary lateral branches: Approximately 30.6 cm.
Diameter of lateral branches: Approximately 3.61 cm.
Quantity of lateral branches: About 15.
Stem:
- *Diameter*.—Approximately 0.8 cm.
- *Color*.—Near Greyed-Purple group RHS N186C.
- *Texture/pubescence*.—Glabrous.
- *Shape*.—Quadrangular.

Internode length: Approximately 5.46 cm.

FOLIAGE

Leaf:
- *Arrangement*.—Opposite.
- *Quantity*.—Approximately 10-14 sets of leaves per main branch.
- *Average length*.—Approximately 5.75 cm. (mature leaf).
- *Average width*.—Approximately 3.6 cm. (mature leaf).
- *Shape of blade*.—Ovate.
- *Apex*.—Acute.
- *Base*.—Cuneate.
- *Attachment*.—Petiolate.
- *Margin*.—Crenate.
- *Texture of top surface*.—Glabrous.
- *Pubescence*.—Absent.
- *Color*.—Young foliage upper side: Near Yellow-Green Group RHS 146B. Young foliage under side: Near Yellow-Green Group RHS 146D. Mature foliage upper side: Near Yellow-Green Group RHS 147A. Mature foliage under side: Near Yellow-Green Group RHS 147C.
- *Venation*.—Type: Pinnate. Venation color upper side: Near Yellow-Green Group RHS 147C. Venation color under side: Near Greyed-Purple group RHS N186D.
- *Petiole*.—Average Length: Approximately 3.09 cm. Diameter: Approximately 3 mm. Color: Near Greyed-Purple group RHS N186C.

FLOWER

Natural flowering season: Mid Spring to Mid Autumn (Fall).
Inflorescence type and habit: Raceme.
Flower longevity on plant: Individual flower approximately 4 to 7 days.
Quantity of flowers: About 15 to 20 buds and 3 to 6 fully opened flowers per lateral branch, at one time; or about 10 blooming spikes per plant.
Inflorescence size:
- *Diameter*.—Approximately 4.6 cm.
- *Height*.—Approximately 25.5 cm.

Peduncle:
- *Length*.—7.2 cm.
- *Diameter*.—0.2 cm.
- *Color*.—Near Greyed-Purple group RHS N186C.
- *Orientation*.—Erect.
- *Strength*.—Strong.

Petals:
- *Petal arrangement*.—Fused into a corolla tube, emerging with asymmetrical upper and lower lips.
- *Corolla tube color*.—Near Red group RHS 54A and 53C.
- *Corolla length*.—4.6 cm.
- *Corolla width*.—1.6 cm. (including lower lip).
- *Corolla tube surface*.—Pubescent.
- *Corolla lip number*.—2.
- *Upper lip shape*.—1 hooded orbicular lip.
- *Upper lip color*.—Near Red group RHS 53C.
- *Upper lip surfaces*.—Pubescent.
- *Upper lip length*.—1.4 cm.
- *Upper lip length*.—0.8 cm.
- *Upper lip apex*.—Obtuse.
- *Margin*.—Entire.
- *Corolla lower lip shape*.—3 lobed.
- *Lower lip base*.—Basally fused.
- *Lower lip apex*.—Obtuse.
- *Lower lip surfaces*.—Glabrous.
- *Corolla lower lip color*.—Upper surface: Near Red group RHS 43B.
- *Corolla lower lip color*.—Lower surface: Near Red group RHS 41B.
- *Lower lip length*.—1.12 cm.
- *Lower lip width*.—1.36 cm.
- *Margin*.—Entire.
- *Petaloids*.—Not present.

Bud:
- *Shape*.—Oblanceolate.
- *Length*.—2.1 cm.
- *Diameter*.—0.8 cm.
- *Color*.—Near Red group RHS 53A.
- *Texture*.—Pubescent.

Calyx:
- *Shape*.—Fused, oblanceolate.
- *Length*.—Approximately 2.23 cm.
- *Width*.—Approximately 0.79 cm.
- *Texture*.—Pubescent.
- *Color*.—Near Greyed-Red group RHS 180A and 180B.

Sepals:
- *Type*.—Fused.
- *Apex*.—Acute.
- *Margin*.—Entire.
- *Texture*.—Pubescent.

Bracts:
- *Shape*.—Elliptic.
- *Apex*.—Acuminate.
- *Margin*.—Entire.
- *Color*.—Near Greyed-Red group RHS 180D to 179D.

*Texture*.—Smooth.
*Shape*.—Concave.

REPRODUCTIVE ORGANS

Stamens:
*Number*.—2.
*Filament length*.—Approximately 1.95 cm.
Anthers:
*Shape*.—Elliptical.
*Length*.—Approximately 3.8 mm.
*Color*.—Near Greyed-Purple group RHS 185D.
*Pollen*.—Absent.
Pistil:
*Number*.—1.
*Length*.—Approximately 4.8 cm.
*Style*.—Length: Approximately 0.4 cm. Color: Near Red-Purple group RHS 67C to Near White group RHS N155C.
*Stigma*.—Shape: 2 lobed. Color: Near Red-Purple group RHS 67C. Ovary color: Near Yellow-Green group RHS 153D (lighter than).

OTHER CHARACTERISTICS

Seeds and fruits: None observed to date.
Disease/pest resistance: Typical for *Salvia*.

What is claimed is:

1. A new and distinct cultivar of *Salvia* hybrid plant named 'SAL010-1' as herein illustrated and described.

* * * * *